(12) United States Patent
Jones, Jr. et al.

(10) Patent No.: US 7,245,759 B2
(45) Date of Patent: Jul. 17, 2007

(54) METHOD OF INSPECTING THREADED FASTENERS AND A SYSTEM THEREFOR

(75) Inventors: James D. Jones, Jr., Barrington, IL (US); Daniel A. Dechant, Darlington, WI (US)

(73) Assignee: Illinois Tool Works Inc, Glenview, IL (US)

( * ) Notice: Subject to any disclaimer, the term of this patent is extended or adjusted under 35 U.S.C. 154(b) by 869 days.

(21) Appl. No.: 10/698,045

(22) Filed: Oct. 30, 2003

(65) Prior Publication Data

US 2005/0094867 A1    May 5, 2005

(51) Int. Cl.
*G06K 9/00* (2006.01)
(52) U.S. Cl. ...................................... 382/152; 382/141
(58) Field of Classification Search ................ 382/152, 382/141
See application file for complete search history.

(56) References Cited

U.S. PATENT DOCUMENTS

| | | | | |
|---|---|---|---|---|
| 3,583,451 A | * | 6/1971 | Dixon et al. | ................ 81/57.37 |
| 5,823,356 A | * | 10/1998 | Goodrich et al. | ............ 209/601 |
| 6,111,601 A | * | 8/2000 | Adachi | ........................ 348/92 |

* cited by examiner

*Primary Examiner*—Matthew C. Bella
*Assistant Examiner*—Mike Rahmjoo
(74) *Attorney, Agent, or Firm*—Mark W. Croll; Paul F. Donovan

(57) ABSTRACT

The present invention relates to novel automated inspection systems and related methods of use. In particular, the present invention provides an automated threaded fastener inspection system, and related methods of use. Furthermore, the present invention provides systems and methods for identifying damaged threaded fasteners prior to industrial use.

19 Claims, 8 Drawing Sheets

METHOD OF INSPECTING THREADED FASTENERS AND A SYSTEM THEREFOR

FIELD OF THE INVENTION

The present invention relates to automated inspection systems and methods of inspection. In particular, the present invention provides a threaded fastener inspection system, and related inspection methods. Furthermore, the present invention provides systems and methods for identifying damaged threaded fasteners prior to their industrial use.

BACKGROUND

Threaded fasteners are used for many applications and must be transported during manufacture and use. During transit and processing, threaded fasteners may become damaged. For example, within a large batch of threaded fasteners, a small number of threaded fasteners may suffer thread damage as they come into contact with other fasteners or with handling equipment. The use of damaged threaded fasteners can result in a defective and potentially unsafe product.

Damaged threaded fasteners are particularly costly for automobile manufacturers. Assembly of automobile engines relies upon threaded fasteners to seal critical engine components. The use of damaged threaded fasteners can result in an improperly sealed engine that is prone to fluid leaks. Automobile manufacturers and suppliers implement post production inspection equipment to locate defective parts such as threaded fasteners. However, post production removal of fasteners is expensive as the engine may need to be disassembled and reassembled. As such, it is desirable to locate defective fasteners prior to assembly.

One inspection technique currently used is a manual inspection of each threaded fastener prior to its use within part assembly. This technique suffers from many problems. Notably, this technique is very expensive, slow, and suffers from human error.

A second inspection technique currently used involves the use of a camera to photograph the threads of a threaded fastener. One problem with this approach is that the camera is unable to capture the entire thread of the threaded fastener. Only a single profile is generally observed. If a thread defect is oriented away from the photographic range of the camera, it will remain undetected.

Accordingly, what is needed in the art are systems and methods for identifying damaged threaded fasteners prior to incorporation into an assembled product.

SUMMARY

The present invention relates to automated inspection systems and methods of inspection. In particular, the present invention provides a threaded fastener inspection system, and related inspection methods. Furthermore, the present invention provides systems and methods for identifying damaged threaded fasteners prior to their industrial use.

Accordingly, the present invention provides a threaded fastener inspection system. In preferred embodiments the threaded fastener inspection system comprises a conveyor, at least one imaging device, and a computer processor. In some embodiments, the imaging device images threaded fasteners at a plurality of views during rotation of a threaded fastener along the conveyor. In further embodiments, the computer processor interfaces with the imaging device. In further embodiments, the computer processor is programmed to analyze the major and minor diameters of the threaded fastener at said plurality of views and compare said major and minor diameters to predetermined values to detect threaded fastener damage.

In further preferred embodiments, the conveyor comprises a rail and a belt. In some embodiments, a portion of said belt is aligned along the length of the rail so that threaded fasteners are secured between the belt and the rail and so that movement of the belt results in the rotation of a threaded fastener along the rail. In preferred embodiments, the rail is a spring loaded rail.

In other preferred embodiments, the imaging device captures an image of threaded fasteners for each 30 degree rotation a threaded fastener makes as it travels within the range of view of the imaging device. In preferred embodiments, the imaging device is stationary.

In some preferred embodiments, the conveyor further comprises a distal end and a sorter, wherein the sorter is positioned at the distal end of the conveyor and wherein the sorter is activated when the computer processor identifies a defective threaded fastener so that damaged threaded fasteners are sorted from undamaged threaded fasteners. In further embodiments, the sorter is a trapdoor. In even further embodiments, the threaded fasteners identified as damaged are discarded into the sorter.

In further preferred embodiments, an illumination device is oriented opposite of the imaging device.

In some embodiments, the present invention provides a threaded fastener head damage inspection system in combination with the thread inspection system, wherein the head damage inspection system comprises a rotating tray having a plurality of openings therein for receiving threaded fasteners and at least one head damage imaging device, wherein the at least one head damage imaging device images the threaded fasteners, and a head damage computer processor interfaced with the head damage imaging device, wherein the head damage computer processor is programmed to analyze the threaded fastener heads of the threaded fasteners and compare the threaded fastener heads to default limits to detect threaded fastener head damage.

In some embodiments, the threaded fasteners are securable within the plurality of openings so that the threaded fastener head is exposed. In further embodiments, the conveyor is positioned to accept threaded fasteners exiting from the threaded fastener head damage inspection system. In even further embodiments, the threaded fastener head damage is selected from the group consisting of cracks, splits, and improper sealing.

The present invention further provides a method of identifying damaged threaded fasteners, comprising providing threaded fasteners, rotating said threaded fasteners, imaging the threaded fasteners at a plurality of views during the rotation, determining major and minor diameters of the threaded fasteners at the plurality of views, comparing the major and minor diameters to predetermined values to determine if the threaded fasteners are damaged, and sorting damaged threaded fasteners from undamaged threaded fasteners. In further embodiments, the comparing is performed by a computer processor.

In even further embodiments, the threaded fasteners are rotated on a conveyor. In still further embodiments, the imaging is performed by a digital camera. In some embodiments, the at least one imaging device captures an image of the threaded fasteners for each 30 degrees of rotation a threaded fastener undergoes as said threaded fastener travels within the range of view of said at least one imaging device. In further embodiments, six views are captured.

Other features and advantages of the invention will become apparent to those skilled in the art upon review of the following detailed description, claims and drawings in which like numerals are used to designate like features.

FIGURE DESCRIPTION

FIG. 5A-F illustrate the range of view of an imaging device within the threaded fastener thread damage inspection system.

Figure 6:
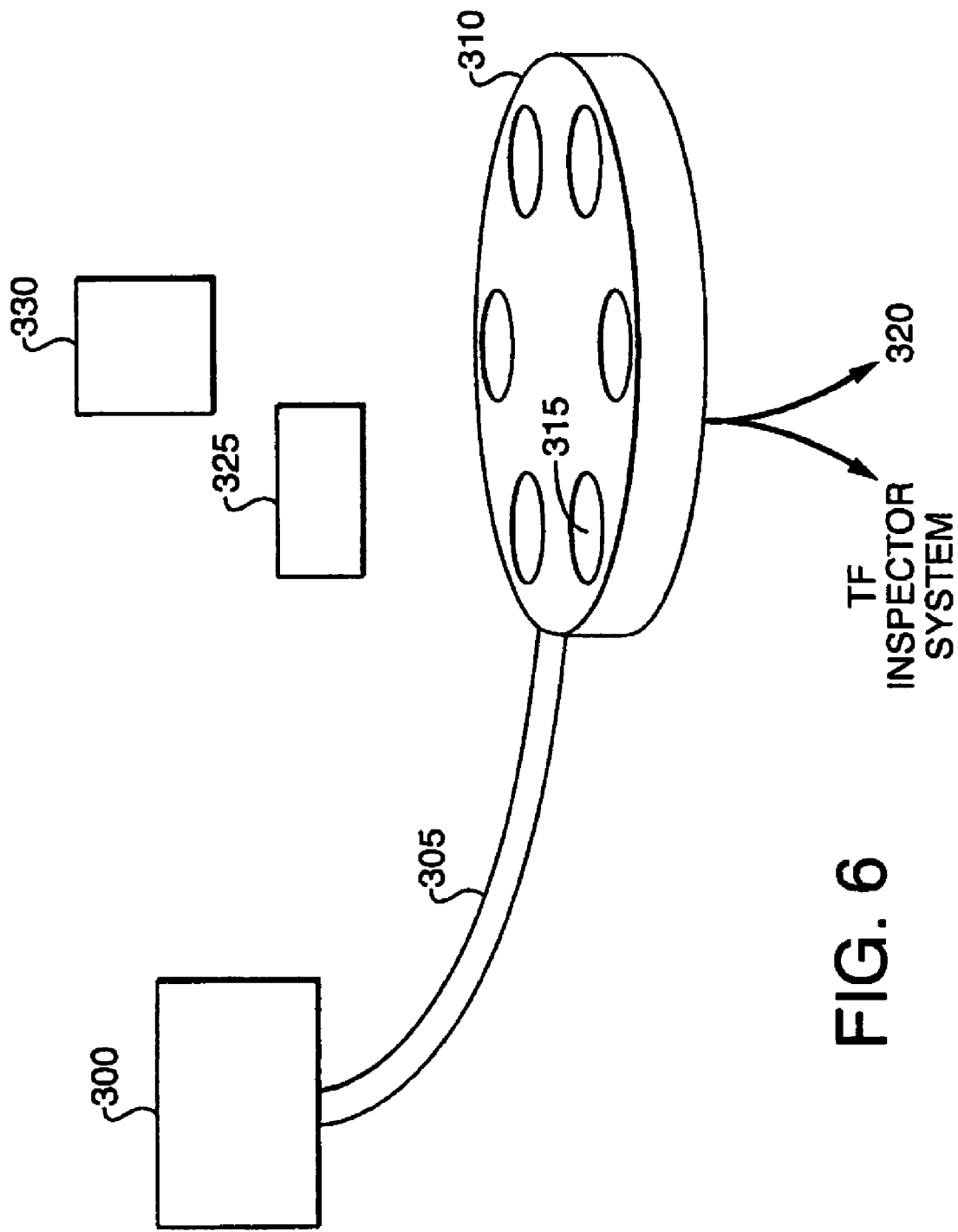

FIG. 6 illustrates a threaded fastener head damage inspection system.

Figure 7:
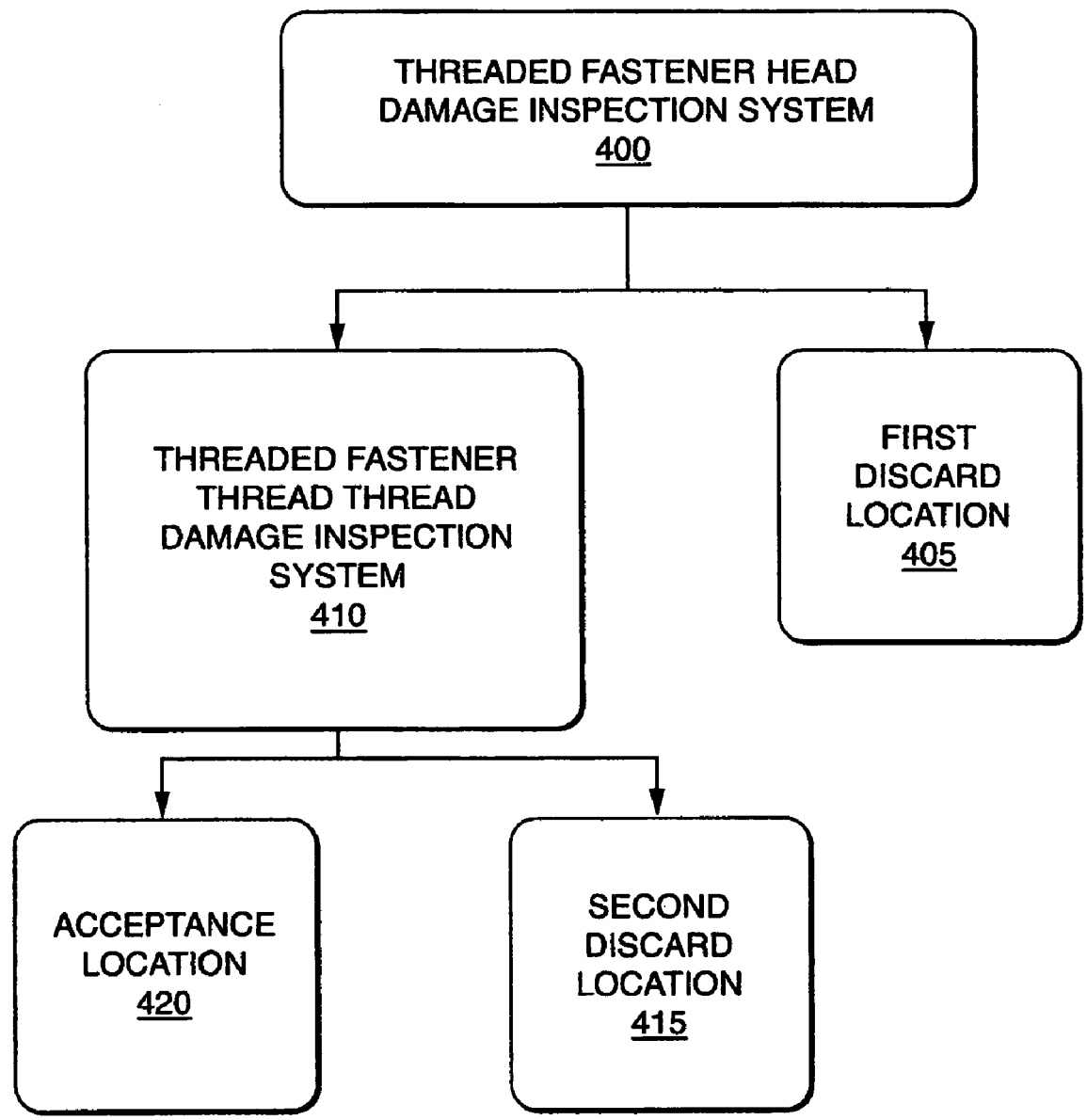

FIG. 7 schematically illustrates a threaded fastener inspection system.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION

The present invention provides inspection systems and methods. The illustrated and preferred embodiments discuss these techniques in the context of threaded fastener inspection systems and methods. However, it should be appreciated that the invention is applicable for use in other inspection applications.

The threaded fastener inspection systems and methods of the present invention have numerous advantages over previous prior art devices including, but not limited to, a faster and more precise approach toward assessing threaded fastener damage. FIGS. 1-7 show various preferred embodiments of the threaded fastener inspection systems and methods of the present invention. The present invention is not limited to these particular embodiments.

The present invention provides systems and methods for detecting thread damage within threaded fasteners. Threaded fasteners refer to hardware agents comprising a threaded face and a head. Examples include, but are not limited to, threaded workpieces, nuts, screws, set screws, grub screws, threaded bolts, and the like.

Figure 1A:
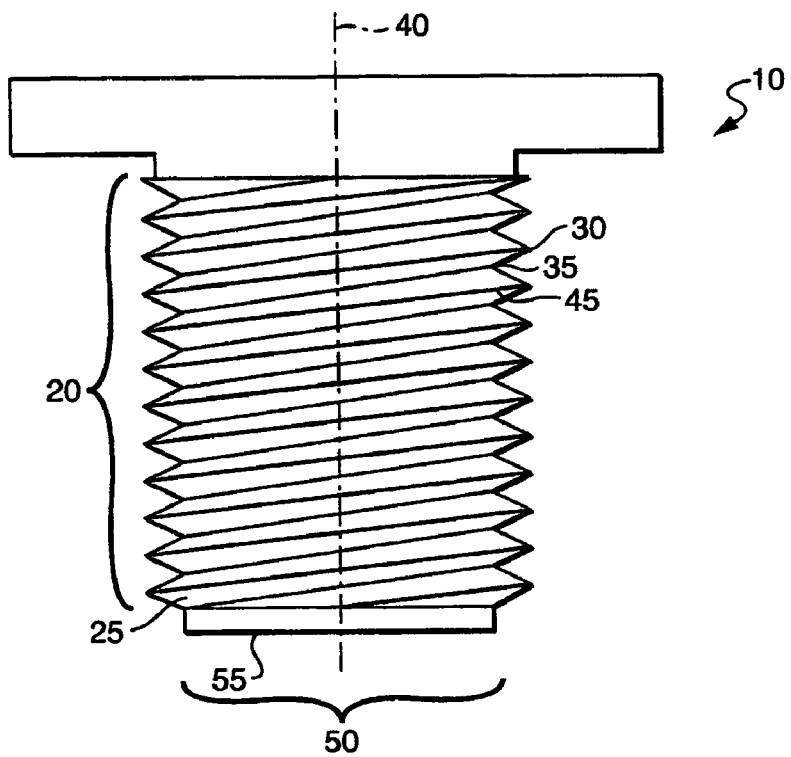
FIG. 1A illustrates an undamaged threaded fastener and FIG. 1B illustrates a damaged threaded fastener.
Figure 1B:
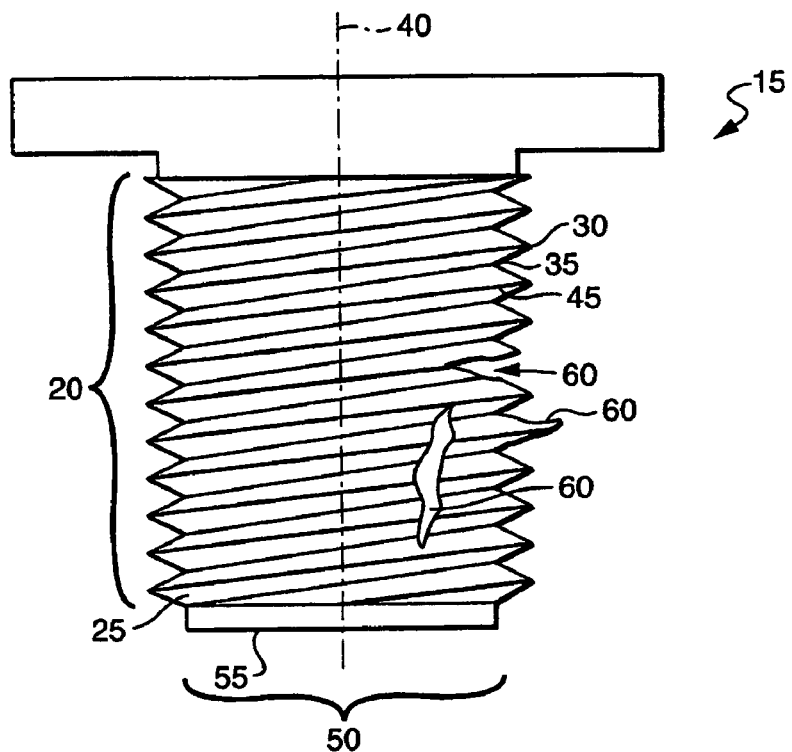

FIG. 1 generally illustrates an undamaged threaded fastener 10 and a damaged threaded fastener 15. A threaded fastener thread face generally comprises a continuous helical ridge 20 formed on the inside (nut) or outside (screw) of a cylinder 25. The apex of the ridge 20 is called the crest 30. Between each crest is a space, called the root 35. Threads are set at an angle to the axis 40 of the bolt or nut. This slope is called the helix angle 45. The helix angle 45 must be sloped, either to the right (for right-hand threaded screws) or the left (for left-hand threaded screws). The threads on a threaded fastener further comprise a major diameter 50 and a minor diameter 55. The major diameter 50 refers to the outside diameter of the thread face and is measured from the outer edge of the crest 30. The minor diameter 55 refers to the inside diameter of the thread face and is measured from the outer edge of the root 35. An undamaged threaded fastener 10 has predetermined or default undamaged major diameter 50 and minor diameter 55 distances. A threaded fastener with damaged threads will have major diameter 50 and minor diameter 55 distances inconsistent with the default undamaged major diameter 50 and minor diameter 55 distances. Referring to FIG. 1, the damaged threaded fastener 55 has a blemish 60 (e.g., a nick or a strip in the thread face) within the thread face. The blemish 60 results in a major diameter 50 distance inconsistent with the undamaged threaded fastener 10 major diameter 50 distance.

The present invention provides systems and methods wherein threaded fasteners are rotatably transported during inspection. Rotatable transport of a threaded fastener refers to rotation of the threaded face along a surface (e.g., rail) resulting in the movement of the threaded fastener along the surface. The thread face may be rotated clockwise or counterclockwise depending on the desired direction of transport. Rotatable transport of a threaded fastener is not limited to a particular speed of transport. In addition, a threaded fastener may be rotatably transported such that the thread head is positioned above, below, or along the direction of transport.

Figure 2:
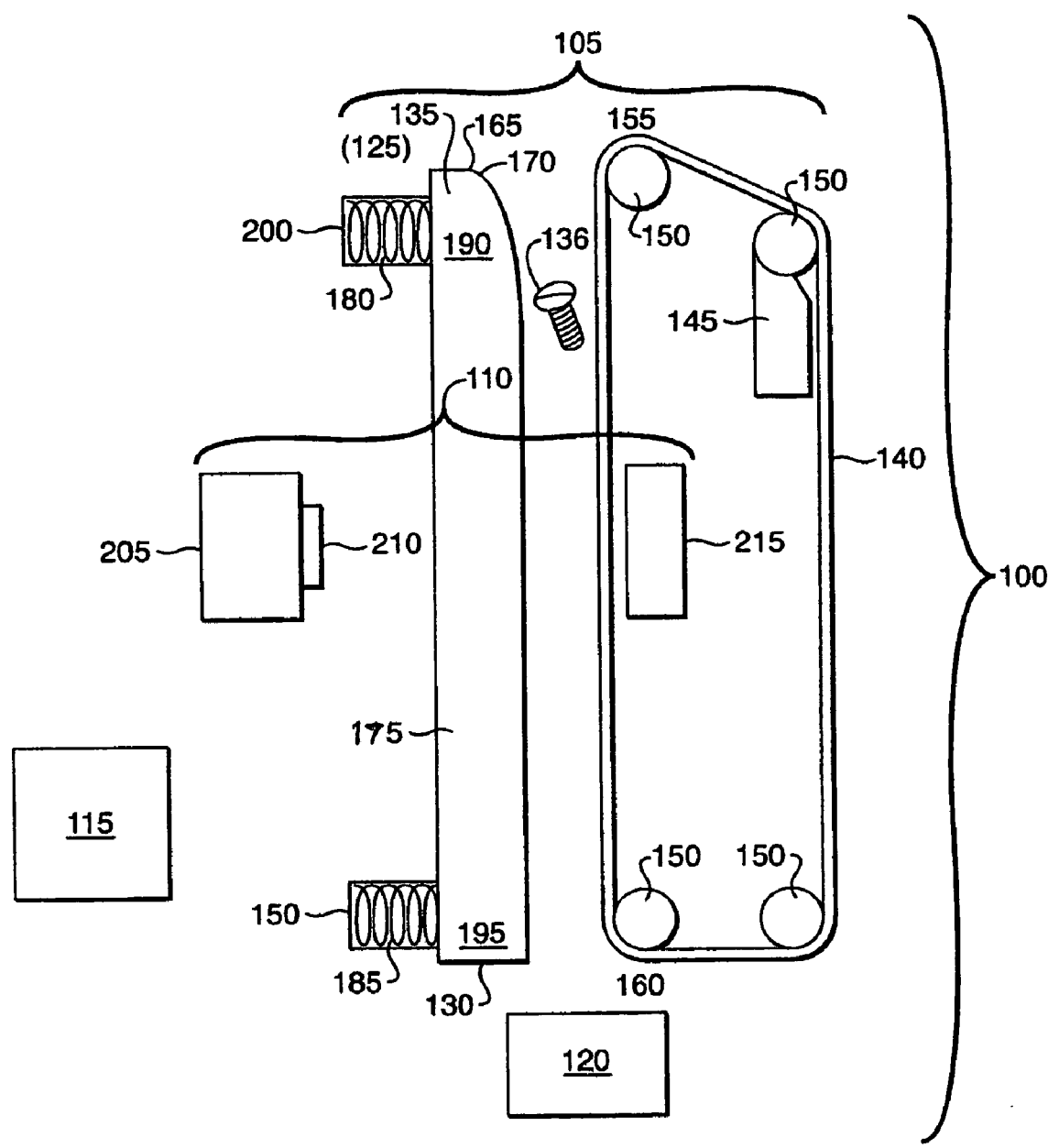
FIG. 2 illustrates a threaded fastener thread damage inspection system.

FIG. 2 illustrates an inspection system 100 of the present invention. In preferred embodiments, the inspection system 100 comprises a conveyor 105, an inspection area 110, a computer processor 115, and a sorter 120.

The conveyor 105 of the present invention rotatably transports threaded fasteners. A conveyor 105 may be driven automatically or manually. In preferred embodiments, the conveyor 105 is driven by an electric motor 145. In some embodiments, the conveyor 105 is positioned at an incline from the conveyor proximal end 125 to the conveyor distal end 130. The conveyor 105 may operate at any desired speed of transport. The conveyor 105 is not limited to a particular length. In preferred embodiments, the conveyor 105 comprises a rail 135 and a belt 140.

In preferred embodiments, the rail 135 comprises any type of material (e.g., steel, metal, plastic, wood) or mixture of such materials. The rail 135 is not limited to a particular length or width. In preferred embodiments, the width of the rail 135 is small in comparison to the length of the threaded fastener so that only a small portion of the face of the threaded fastener is obscured by the rail 135. In preferred embodiments, the rail 135 is a spring loaded rail.

In preferred embodiments, the rail 135 is a spring loaded rail 175. In some embodiments, the spring loaded rail 175 comprises at least one spring 180 and 185. In some embodiments, the spring 180 is positioned around a cylinder 200. The cylinder 200 can comprise any type of material (e.g., metal, plastic) or any mixture of such materials. The cylinder 200 is not limited by a particular length or width. The springs 180 and 185 may be adjusted to create a desired tension. In preferred embodiments, the spring loaded rail 175 contains two springs 180 and 185. In further embodiments, the two springs 180 and 185 are positioned at the proximal end 190 and the distal end 195 of the spring loaded rail 175. In even further embodiments, the two springs 180 and 185 are positioned across from rollers 150 positioned at the proximal and distal ends of the belt 140.

The belt 140 can preferably comprise any type of material (e.g., rubber, metal, leather, plastic) or mixture of such materials. The belt 140 may be driven automatically or manually. In preferred embodiments, the belt 140 is driven by a motor 145. The belt 140 is not limited to a particular length or width. In preferred embodiments, the belt 140 is approximately ¼ inch thick. In some embodiments, a fixed shape is maintained in the belt 140 through a plurality of rollers 150. In preferred embodiments, rollers 150 are positioned at the belt proximal end 155 and the belt distal end 160 of the belt 140.

In preferred embodiments, threaded fasteners 136 are rotatably transported in between the rail 135 and the belt 140. The belt 140 is positioned along the rail 135. A threaded fastener 136 enters the conveyor 105 at the proximal end 165 of the rail 135. In some embodiments, the proximal end 165 of the rail 135 is rounded 170 to facilitate the entrance of threaded fastener 136 in between the rail 135 and the belt 140.

Figure 3:
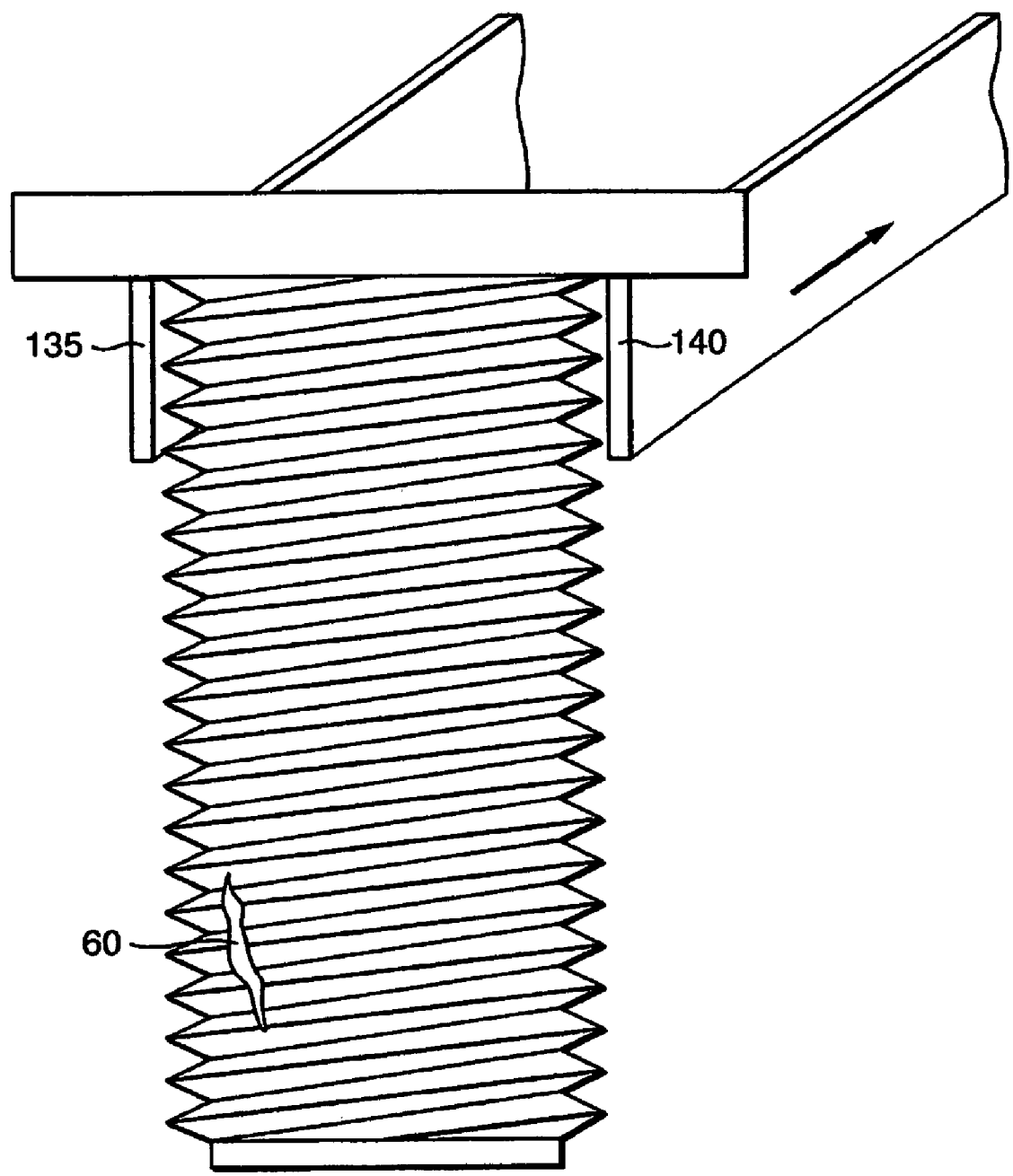
FIG. 3 illustrates a threaded fastener in the threaded fastener thread damage inspection system of FIG. 2.

FIG. 3 illustrates a threaded fastener in between the rail 135 and the belt 140. The upper end of the threaded fastener thread face is positioned in between the rail 135 and the belt 140. The head of the threaded fastener is positioned above the rail 135 and the belt 140. The movement of the belt 140 results in the threaded fastener transporting along the rail 135. Alternatively, the head of the threaded fastener can ride on a pair of spaced apart rails with the belt 140 being located beneath one of the rails.

Returning to FIG. 2, the inspection area 110 comprises an imaging device 205 and an illumination device 210. The imaging device 205 (e.g., digital camera) may further be positioned anywhere along the length of the rail 135. The imaging device 205 may be held in a stationary position or may be mobile. In preferred embodiments, the imaging device 205 is stationary. The present invention is not limited to any particular type of imaging device 205. Furthermore, the imaging device 205 may be adjusted to accommodate imaging of threaded fasteners of various sizes and shapes.

The inspection area 110 further comprises an illumination device 215 (e.g., light bulb). The illumination device 215 is not limited to any particular strength (e.g., wattage). In some embodiments, the illumination device 215 is positioned beneath the belt 140 so that a threaded fastener traveling along the conveyor 105 is back-lit. The illumination device 215 is further positioned directly across from the imaging device 205.

Figure 4:
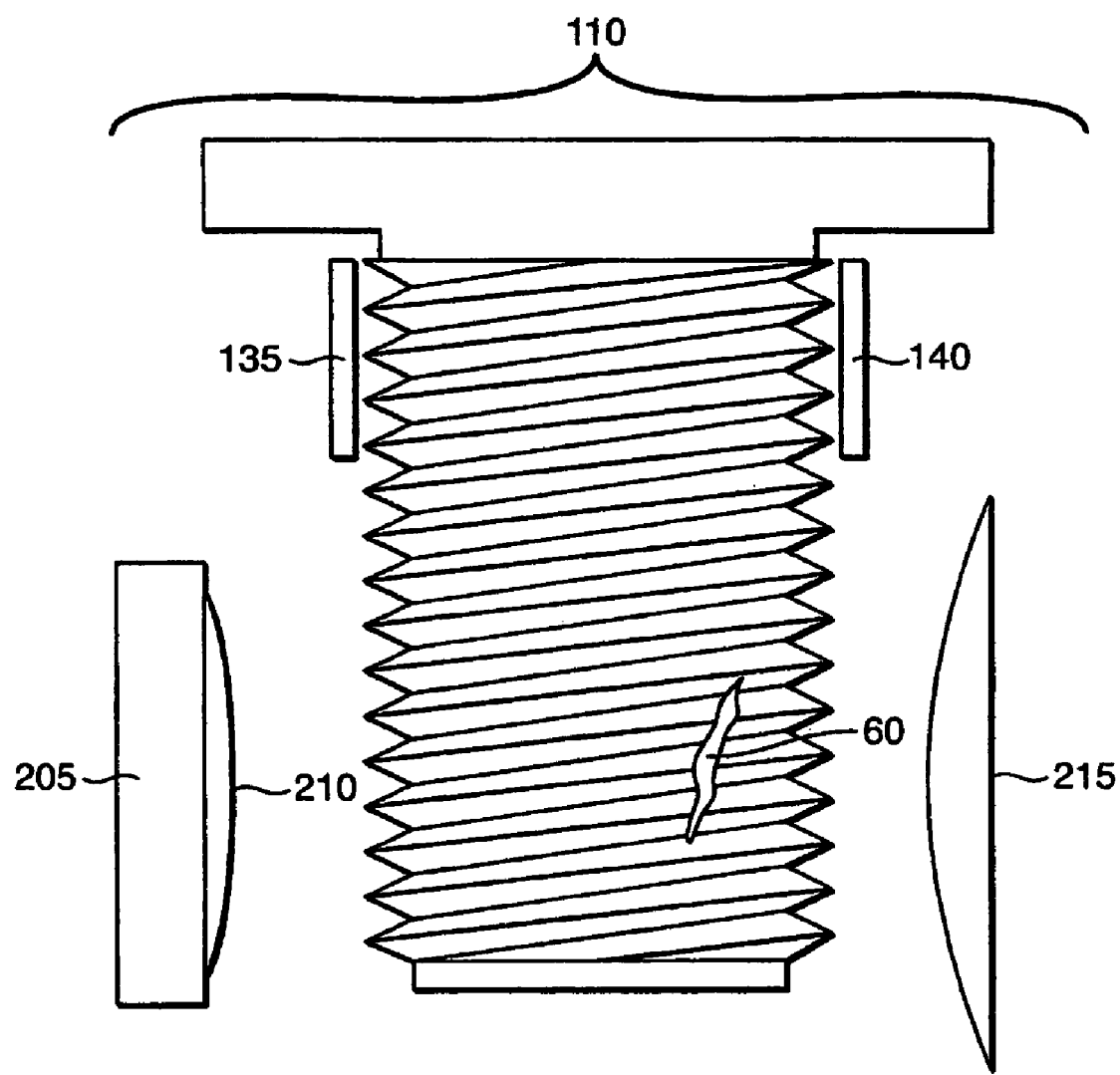
FIG. 4 illustrates the inspection area of the threaded fastener thread damage inspection system.
Figure 5C:
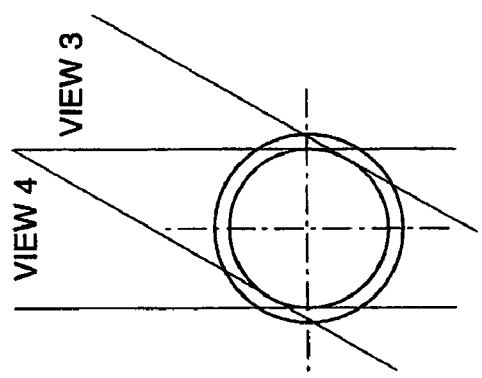
Figure 5B:
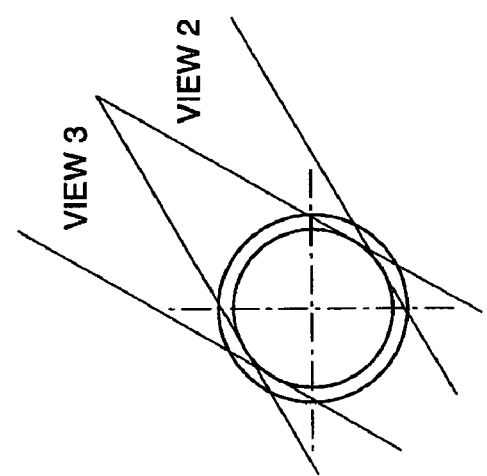
Figure 5A:
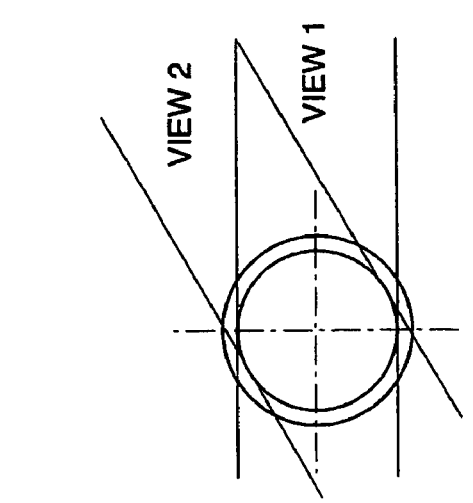
Figure 5F:
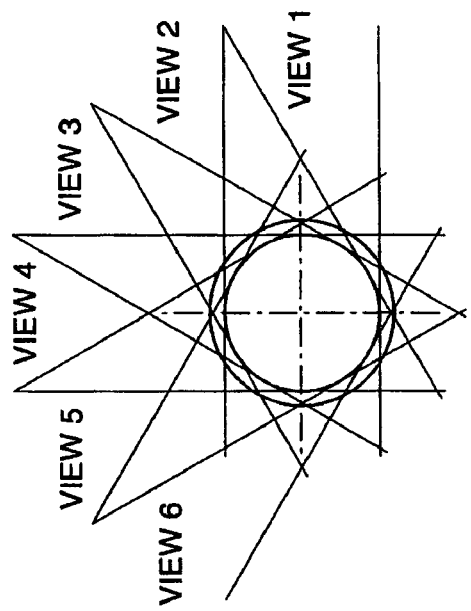
Figure 5E:
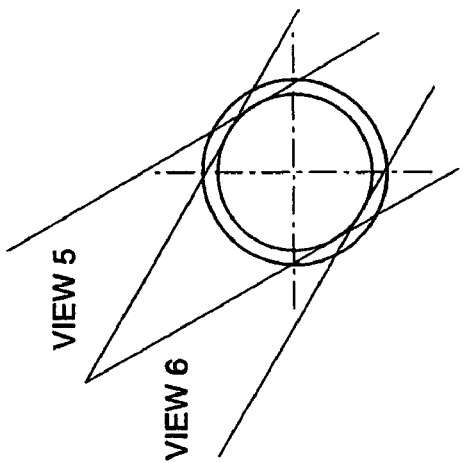
Figure 5D:
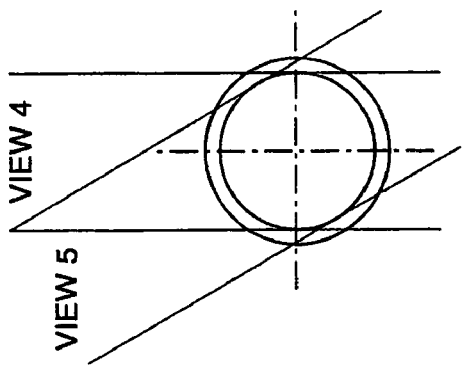

FIG. 4 illustrates a threaded fastener within an inspection area 110. An imaging device 205 (e.g., digital camera) is positioned below the rail 135. In preferred embodiments, the imaging device 205 is positioned so that the upper end of the imaging device lens 210 is positioned in line with the lowest point of the rail 135. As discussed above, a threaded fastener positioned between the rail 135 and belt 140 will have the majority of its threaded face exposed beneath the rail 135 and belt 140. The imaging device lens 210 is further positioned so as to be within view of the exposed threaded face, preferably the entire exposed threaded face, of a threaded fastener positioned between the rail 135 and belt 140.

The present invention is configured to image the thread face of a threaded fastener traveling along the rail 135. In preferred embodiments, a rotating threaded fastener passing within the range of view of the imaging device 205 will expose at least half (e.g., 180 degrees) of its face to the imaging device lens 210. It will be recognized that the speed of the motor 145 can be varied to vary the speed of the belt 140 and thus the speed of rotation of the threaded fastener. The imaging device 205 is configured to capture a plurality of images of the thread face of a threaded fastener rotating along the rail 135. In preferred embodiments, the imaging device 205 is programmed according to this speed of rotation so that it can capture an image of the threaded fastener for each 30 degree rotation the threaded makes as it travels within the range of view of the imaging device lens 210. As illustrated in FIG. 5, in preferred embodiments the imaging device 205 captures images of the entire (e.g., 360 degree) face of a rotating object if six images are compiled of the rotating object at six successive 30 degree intervals. In addition, six images of a rotating object taken at six successive 30 degree increments ensures that overlapping profiles of the face of the rotating object are captured. Other angles can be used, so long as the increments provide an overlapping profile of the face of the rotating object being captured.

In preferred embodiments, the imaging device 205 is configured to capture six images of the thread face of a threaded fastener rotating along the rail 135. In further preferred embodiments, the imaging device 205 is configured to capture six images of the thread face of a threaded fastener at six successive 30 degree intervals as the threaded fastener rotates along the rail 135.

In preferred embodiments, the imaging device 205 provides images of the thread face of a threaded fastener to the computer processor 115. The present invention is not limited to any type of computer processor 115. In some embodiments, the computer processor 115 is a part of the imaging device 205, while in other embodiments, the computer processor 115 is interfaced with imaging device 205 via a computer cable. The computer processor 115 is programmed to detect damaged threaded fastener thread faces by analyzing the images obtained from the imaging device 205 and comparing the data obtained from this analysis with a set of predetermined threaded fastener face criteria. According to one aspect of the invention, the inspection system is looking for the absence of light. If light is present during the inspection process, the system recognizes that a flaw or defect may be present in the threaded fastener. According to another aspect of the invention, default major and minor diameters for undamaged fasteners are compared to the imaged major and minor diameters. Threaded fasteners not meeting the predetermined threaded fastener face criteria are sorted via a sorter 120. In preferred embodiments, the sorter 120 is a trapdoor.

Referring to FIG. 6, in another embodiment of the present invention, an inspection system for detecting threaded fastener head is provided. A bin 300 connects with a chute 305 (e.g., conveyor belt). The chute 305 connects with a rotating tray 310 (e.g., rotating turn table). The rotating tray 310 can be operated at a variety of predetermined speeds. The rotating tray 310 has a therein a plurality of rotating tray openings 315 that receive threaded fasteners from the chute 305. In preferred embodiments, the rotating tray 310 comprises six rotating tray openings 315. In some embodiments, the rotating tray 310 connects with both a discard device 320 and a threaded fastener inspection system (see FIG. 7). In preferred embodiments, at least one head or seal damage imaging device 325 is positioned above the rotating tray 310. In preferred embodiments, the head or seal damage imaging device 325 interfaces with a head or seal damage computer processor 330.

The chute 305 is configured to transfer a plurality of threaded fasteners from the bin 300 into available (e.g., empty, unoccupied) rotating tray openings 315. In preferred embodiments, the rotating tray openings 315 are configured to secure the thread face of threaded fasteners thereby leaving the heads of secured threaded fasteners exposed.

Threaded fastener heads may be damaged in numerous manners (e.g., cracked heads, unsealed heads, split heads). In preferred embodiments, the head or seal damage imaging device 325 is positioned above the rotating tray 310 so as to facilitate the capturing of a plurality of images of the heads of threaded fasteners secured within rotating tray openings 315. The head or seal damage imaging device 325 further provides such images of the heads of threaded fasteners to the head or seal damage computer processor 330. The head or seal damage computer processor 330 is programmed with predetermined undamaged threaded fastener head criteria. In preferred embodiments, the head or seal damage computer processor 330 implements a program to compare the image of a threaded fastener head with the predetermined undamaged threaded fastener head criteria. As such, the head or seal damage computer processor 330 is programmed to analyze digital images captured by the head or seal damage imaging device 325 to detect damaged threaded fastener heads. According to another aspect of the invention, the inspection system is looking for the absence of light. If light is present during the inspection process, the system recognizes that a flaw or defect may be present in the threaded fastener head. In preferred embodiments, threaded fastener heads meeting the predetermined undamaged threaded fastener head criteria are provided to a threaded fastener inspection system (discussed above). Threaded fastener heads not meeting the predetermined criteria are provided to the discard device 320.

FIG. 7 schematically illustrates a threaded fastener inspection system embodiment for inspecting a plurality of threaded fasteners. In particular, a threaded fastener head damage inspection system 400 interfaces with a first discard location 405 and/or a threaded fastener thread damage inspection system 410. The threaded fastener thread damage inspection system 410 interfaces with either a second discard location 415 or an acceptance location 420. The present invention is not limited to a particular threaded fastener inspection system configuration. Indeed, in some embodiments the present invention provides only a threaded fastener head damage inspection system 400 or only a threaded fastener thread damage inspection system 410. In preferred embodiments, the present invention provides both a threaded fastener head damage inspection system 400 and a threaded fastener thread damage inspection system 410.

Variations and modifications of the foregoing are within the scope of the present invention. It is understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention. The claims are to be construed to include alternative embodiments to the extent permitted by the prior art.

Various features of the invention are set forth in the following claims.

What is claimed is:

1. A threaded fastener inspection system comprising: a conveyor; at least one imaging device, wherein said at least one imaging device images said threaded fasteners at a plurality views during rotation of said threaded fastener along said conveyor; and a computer processor interfaced with said imaging device, wherein said computer processor is programmed to recognize and detect threaded fastener damage; wherein said conveyor comprises: a rail; and a belt, wherein a portion of said belt is aligned along the length of said rail so that said threaded fasteners are secured between said belt and said rail and so that movement of said belt results in the rotation of said threaded fastener along said rail; and wherein said rail is a spring loaded rail; and wherein said at least one imaging device captures overlapping images of said threaded fasteners as said threaded fastener travels within the range of view of said at least one imaging device.

2. The system of claim 1, wherein said computer processor is programmed to analyze the major and minor diameters of said threaded fastener at said plurality of views and compare said major and minor diameters to predetermined values to detect threaded fastener damage.

3. The system of claim 1, wherein said at least one imaging device captures six images of said threaded fasteners, one for each 30 degree rotation said threaded fastener makes, as it travels within the range of view of said at least one imaging device.

4. The system of claim 1, wherein said at least one imaging device is stationary.

5. The system of claim 1, wherein said conveyor further comprises a distal end and a sorter, wherein said sorter is positioned at said distal end of said conveyor and wherein said sorter is activated when said computer processor identifies a defective threaded fastener so that damaged threaded fasteners are sorted from undamaged threaded fasteners.

6. The system of claim 5, wherein said sorter is a trapdoor.

7. The system of claim 6, wherein said threaded fasteners identified as damaged are discarded into said sorter.

8. The system of claim 1, further comprising an illumination device oriented opposite of said imaging device.

9. The system of claim 1, further comprising a threaded fastener head damage inspection system, wherein said head damage inspection system comprises:
a rotating tray having a plurality of openings therein for receiving threaded fasteners;
at least one head damage imaging device, wherein said at least one head damage imaging device images said threaded fasteners; and
a head damage computer processor interfaced with said head damage imaging device, wherein said head damage computer processor is programmed to analyze the threaded fastener heads of said threaded fasteners and compare said threaded fastener heads to default limits to detect threaded fastener head damage.

10. The system of claim 9, wherein said threaded fasteners are securable within said plurality of openings so that the threaded fastener head is exposed.

11. The system of claim 9, wherein said conveyor is positioned to accept threaded fasteners exiting from said threaded fastener head damage inspection system.

12. The system of claim 9, wherein said threaded fastener head damage is selected from the group consisting of cracks, splits, and improper sealing.

13. A threaded fastener inspection system comprising: a conveyor, comprising: a rail; and a belt, wherein a portion of said belt is aligned along the length of said rail so that said threaded fasteners are secured between said belt and said rail and so that movement of said belt results in the rotation of said threaded fastener along said rail; at least one imaging device, wherein said at least one imaging device images said threaded fasteners at a plurality views during rotation of said threaded fastener along said conveyor; a computer processor interfaced with said imaging device, wherein said computer processor is programmed to recognize and detect threaded fastener damage; and a sorter positioned at the distal end of said conveyor, wherein said sorter is activated when said computer processor identifies a defective threaded fastener so that damaged threaded fasteners are sorted from undamaged threaded fasteners; wherein said computer processor is programmed to analyze the major and minor diameters of said threaded fastener at said plurality of views and compare said major and minor diameters to predetermined values to detect threaded fastener damage.

14. A method of identifying damaged threaded fasteners, comprising: providing threaded fasteners; rotating said threaded fasteners; imaging said threaded fasteners at a plurality of views during said rotation; analyzing said views to determine if said threaded fasteners are damaged; and sorting damaged threaded fasteners from undamaged threaded fasteners; wherein said imaging step includes capturing overlapping images of said threaded fasteners as said threaded fastener travels within the range of view of said at least one imaging device;

wherein said imaging step includes capturing six images of said threaded fasteners, one for each 30 degrees of rotation said threaded fastener undergoes, as said threaded fastener travels within the range of view of said at least one imaging device.

15. The method of claim 14, further comprising the steps of:

determining major and minor diameters of said threaded fasteners at said plurality of views; and comparing said major and minor diameters to predetermined values to determine if said threaded fasteners are damaged.

16. The method of claim 14, wherein said imaging step includes imaging heads of the threaded fasteners.

17. The method of claim 14, wherein said comparing is performed by a computer processor.

18. The method of claim 14, wherein said threaded fasteners are rotated on a conveyor.

19. The method of claim 14, wherein said imaging is performed by a digital camera.

* * * * *